United States Patent [19]

Olofson et al.

[11] 4,141,897

[45] Feb. 27, 1979

[54] N-DEALKYLATION OF N-ALKYL-14-HYDROXYMORPHINANS AND DERIVATIVES THEREOF

[75] Inventors: Roy A. Olofson, State College, Pa.; Joseph P. Pepe, Rochester, N.Y.

[73] Assignee: Research Corporation, New York, N.Y.

[21] Appl. No.: 751,570

[22] Filed: Dec. 20, 1976

[51] Int. Cl.$^2$ .......................................... C07D 489/08
[52] U.S. Cl. ...................................... 546/45; 546/74; 546/46
[58] Field of Search ........................................ 260/285

[56] References Cited

U.S. PATENT DOCUMENTS

| | | | |
|---|---|---|---|
| 3,230,224 | 1/1966 | Sawa et al. | 260/285 |
| 3,254,088 | 5/1966 | Lewenstein et al. | 260/285 |
| 3,285,922 | 11/1966 | Gates, Jr. | 260/285 |
| 3,320,262 | 5/1967 | Lewwnstein et al. | 260/285 |
| 3,828,050 | 8/1974 | Buckett et al. | 260/285 |
| 3,872,127 | 3/1975 | Merz et al. | 260/285 |
| 3,905,981 | 9/1975 | Olofson et al. | 260/285 |

FOREIGN PATENT DOCUMENTS

2208902  6/1974  France .................................. 260/285

*Primary Examiner*—Donald G. Daus
*Assistant Examiner*—Diana G. Rivers
*Attorney, Agent, or Firm*—Omri M. Behr

[57] ABSTRACT

There is provided a novel, high yield, method of dealkylating N-alkylated 14-hydroxymorphinans and derivatives thereof including, inter alia, oxymorphone and oycodone. There are thus provided, inter alia, more efficient routes for the formation of naloxone, naltrexone, and nalbuphine. In the principal step of the process, the dealkylation using certain oxycarbonyl halides (or haloformates) is carried out on the N-alkyl-14-acyloxymorphinan which it is desired to dealkylate.

14 Claims, No Drawings

N-DEALKYLATION OF N-ALKYL-14-HYDROXYMORPHINANS AND DERIVATIVES THEREOF

BACKGROUND OF THE INVENTION (The invention described herein was made under Grant GM 13980 from National Institutes of Health, Department of Health, Education and Welfare.)

It has been found desirable in the field of chemistry dealing with the morphine alkaloids to carry out molecular modifications which will alter the basic characteristics of morphine to obtain compounds which are either substantially non-addicting analgesics or narcotic antagonists or have other desirable properties. One of the major problems in this area has been the removal of the alkyl group, usually the methyl group, from the ring nitrogen and, under certain circumstances, its replacement with alkyl moieties other than the methyl group.

A substantial advance in this art was achieved by one of the co-inventors herein in the work patented by him and other co-workers in U.S. Pat. No. 3,905,981. In this work, it was discovered that vinyl chloroformate and certain derivatives thereof would replace the methyl group on the ring nitrogen, and be removable therefrom under mild conditions which did not adversely affect most of the other labile groups to be found on most of the starting materials in this field which are generally available.

In order that the present application not be too voluminous, the disclosure of the aforementioned U.S. Pat. No. 3,905,981, is incorporated herein by reference. Unfortunately, it was found that where a hydroxy group is present in the 14-position of the morphinan skeleton, the yields in the N-dealkylation step are not satisfactory for commercial purposes (see Example VI of the patent).

It was therefore believed desirable to seek a route by which the vinyl haloformate dealkylation could be applied to 14-hydroxylated compounds in a manner which would give rise to commercially satisfactory yields as well as clean products.

SUMMARY OF THE INVENTION

It has been found that when a N-alkylated, suitably N-methylated, 14-hydroxymorphinan, suitably a 3,14-dihydroxymorphinan, protected at the 3-position, is acylated at the 14 position, it may be readily N-dealkylated using vinyl haloformate. It has been found that other haloformates such as 2,2,2-trichloroethyl chloroformate are also operative. The process of the present invention is operative, as will be shown in more detail hereinbelow, regardless of whether or not a substituent is present at the 3, 4, 5, or 6 positions. Where, for example, a hydroxy group is originally present at the 3 position, this may, if desired, be regenerated together with the hydroxy group at the 14 position after the N-dealkylation step has taken place. The process of the present invention provides, inter alia, more commercially efficient routes to naloxone and naltrexone as well as providing the initial step for a more efficient synthesis of nalbuphine and for another competitive synthesis of naltrexone disclosed and claimed in Applicants' co-pending application filed concurrently herewith.

The process of the present invention may be summarized in the flow sheet set forth hereinbelow.

The flow diagram of structural formulae is of general applicability, the Examples shown however are illustrative and not limiting.

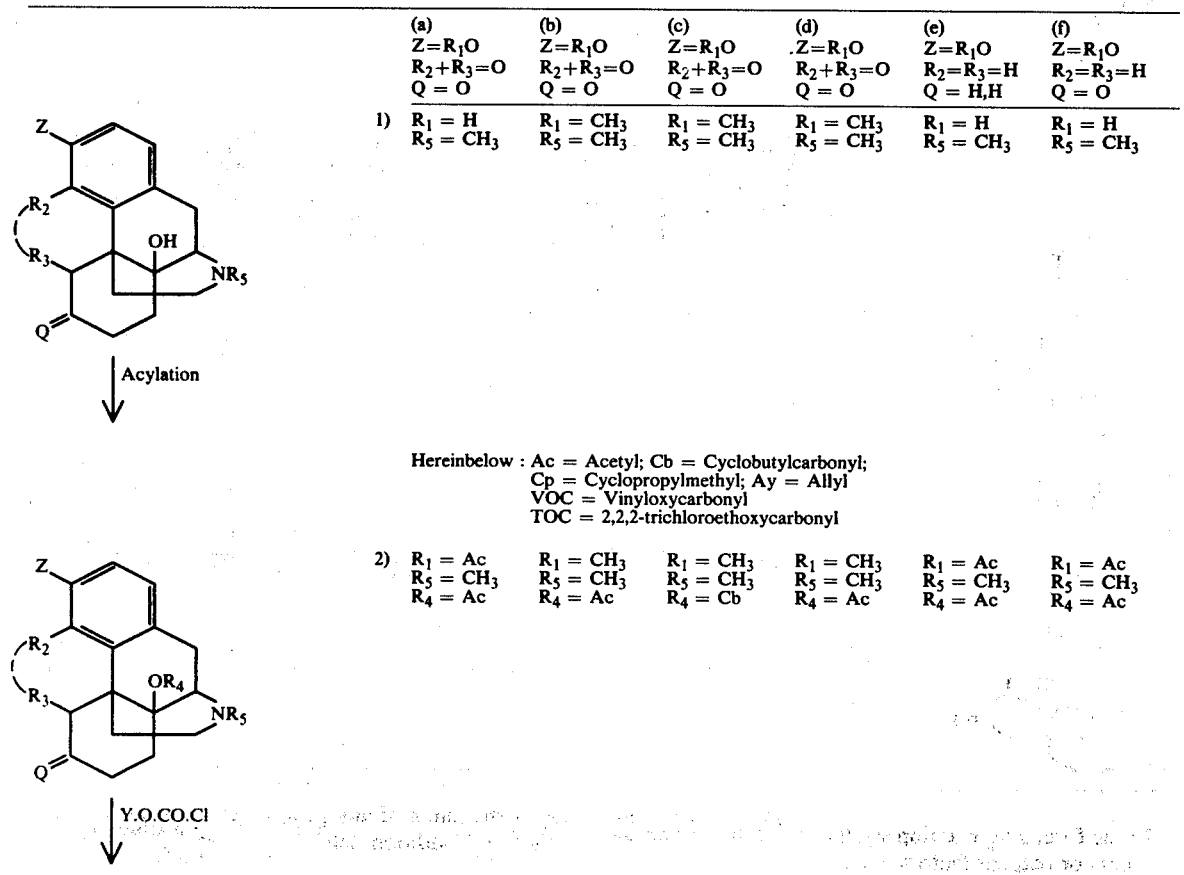

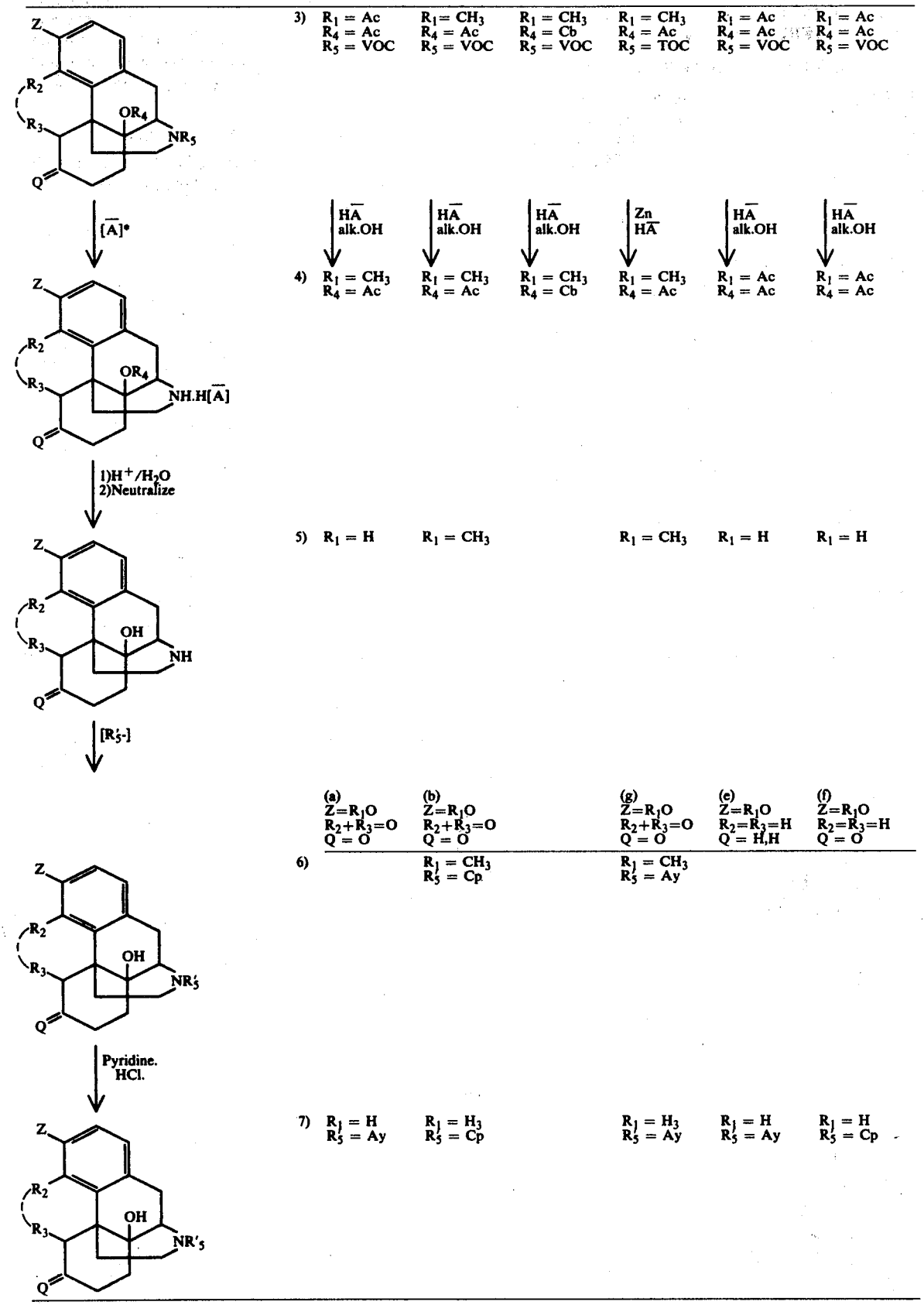
In the foregoing reaction sequence only the common reagents or reagent factors are shown.
[A̅] is the anion of any proton acid capable of forming an acid addition salt with a secondary amine, included are the anions of mineral acids such as halide, suitably chloride or bromide, bisulfate, sulfate, nitrate, phosphate and the like, the anions of organic acids such as carboxylic or lower alkanoic acids such as formates, acetate, propionate and the like, and anions of sulfonic acids, suitably arylsulfonic acids such as benzene or toluene sulfonates and of alkylsulfonic acids such as methanesulfonate.

The foregoing list is not intended to be exhaustive or limiting but merely exemplary.

Z is hydrogen or $R_1O$, $R_1$ is hydrogen, alkanoyl, phenylalkanoyl, substituted phenylalkanoyl, suitably alkyl or polyalkyl phenylalkanoyl, cycloalkylcarbonyl; alkyl; cycloalkyl; cycloalkyl alkyl, phenylalkyl and substituted phenyl loweralkyl;

$R_2$ and $R_3$ may each be hydrogen or when taken together are oxa;

Q is 2 hydrogen atoms or oxo;

$R_4$ is alkanoyl, phenylalkanoyl, substituted phenylalkanoyl, suitably alkyl or polyalkyl phenylalkanoyl, or cycloalkylcarbonyl;

$R_5$ is alkyl, usually methyl;

$R_5'$ is alkyl, usually other than methyl, cycloalkyl, cycloalkyl alkyl, phenylalkyl, allyl, or alkyl substituted allyl.

DESCRIPTION OF THE PREFERRED EMBODIMENTS

In the process of the present invention, there may be used any N-alkylated 14-hydroxymorphinans. While the process of the present invention would be operative for any members of this group, the natural and synthetic compounds to which the process would usually be applied carry a hydroxy or substituted hydroxy group at the 3 position; thus, $R_1$ may be hydrogen, alkanoyl, suitably lower alkanoyl — for example, having 1 to 5 carbon atoms in the alkyl moiety thereof — for example, acetyl, propionyl, butyryl, valeryl, and the like, phenylalkanoyl and substituted phenylalkanoyl suitably phenyl lower alkanoyl such as benzoyl, phenylacetyl, phenylpropionyl, phenylbutyryl, and the like, and as substituted pheyl lower alkanoyls may be included moieties having — for example, alkyl substituents in phenyl nucleus, also included is cycloalkylcarbonyl such as cycloloweralkylcarbonyl of 3 through 6 carbon atoms in the cycloalkyl moiety, including in particular cyclopropyl and cyclobutyl, $R_1$ may also be alkyl, suitably lower alkyl of 1 to 5 carbon atoms such as methyl, ethyl, propyl, butyl, and the like, cycloalkyl of 3–6 carbon atoms such as cyclopropyl, cyclobutyl, cyclopentyl or cyclohexyl, cycloalkyl lower alkyl wherein the cycloalkyl and alkyl, suitably lower alkyl moieties are then set for the immediately hereinabove, or phenylalkyl such as benzyl, phenethyl, phenylbutyl, and the like.

Where $R_1$ is hydrogen the hydroxy group at the 3-position is protected at least in steps 1–4 as shown in the flow sheet by any protecting group known in the art to be stable under the reaction conditions set forth, acylation suitably alkanoylation being most preferred.

$R_2$ and $R_3$ are each hydrogen or when taken together are oxa, Q is either 2 hydrogen atoms or oxo. Thus, in the synthetic morphinan series, $R_1$, $R_2$ and Q are all hydrogen though Q may also be oxo and in the natural series $R_1$ is usually hydrogen or methyl, $R_2$ with $R_3$ is oxa, and Q is oxo. Among the most important starting materials may be mentioned oxymorphone which is utilized in the naloxone and naltrexone syntheses, and oxycodone which is utilized in the naltrexone synthesis, as well as in the nalbuphine synthesis.

$R_5$ is lower alkyl of 1–6 carbon atoms, phenyl lower alkyl having 1–6 carbon atoms in the lower alkyl moiety, cycloalkyl or cycloalkyl lower alkyl of 3–6 carbon atoms in the cyclic moiety and 1–5 carbon atoms in the lower alkyl moiety.

Any readily available acylating agent may be employed in the 14-acylation to give rise to the $R_4$ group. It is preferred to utilize an alkanoylating agent, suitably an acid halide suitably an acid chloride or an acid anhydride giving rise to a lower alkanoyl moiety having 1 to 5 carbon atoms in the alkyl moiety. There may also be included phenyl lower alkanoyl moieties suitably benzoyl, also included are cycloalkylcarbonyl moieties having from 1 to 6 carbon atoms in the cycloalkyl moiety. Especially favored are the acetylating agents such as acetyl chloride or acetic anhydride where it is desired to utilize the acetyl moiety purely as a protecting group. Where it is desired to proceed further to the synthesis of naltrexone or nalbuphine in the manner disclosed in the co-pending application, there is employed an alkanoylating agent generating initially 14-O-cyclobutylcarbonyl and 14-O-cyclopropylcarbonyl moieties such as cyclobutanecarboxylic acid anhydride and cyclopropanecarboxylic acid anhydride.

The acylation at the 14-hydroxy position is carried out by methods well known in the art. Among the suitable methods may be mentioned Lewenstein, British Pat. No. 955,493. In this procedure, the starting material containing the 14-hydroxy group is heated under reflux and agitation in an inert atmosphere, suitably a nitrogen atmosphere, with the alkanoylating agent, suitably with the acid anhydride, if that is the alkanoylating agent of choice. The heating is carried on for from about one to about three hours, suitably for about two hours, at between 80° C. and 120° C., suitably 100° C., and the volatiles removed under reduced pressure.

It is generally not necessary to purify the acylated compound (2). Indeed such a step can reduce the ultimate yields due to hydrolysis loss in the recrystalization step.

The 14-acyloxy-N-alkylated compound (2) wherein the alkyl moiety is usually methyl, is then treated with the appropriate haloformate. Haloformates having the formula

wherein Y is vinyl or substituted vinyl, 2-mono-, di-, or tri haloethyl, suitably 2,2,2-trichloroethyl, and phenyl or substituted phenyl may be employed. The vinyl haloformates which may be employed are more specifically disclosed in U.S. Pat. No. 3,905,981, column 3, lines 4 through 45, which are incorporated herein by reference. Of the haloformates which may be employed in this reaction, the best results have been obtained using vinyl chloroformate itself, although the results obtained using the trichloroethyl chloroformate are almost as good, excluding recoverable starting material.

The reaction between the tertiary amine group and the vinyl chloroformate is generally carried out in a suitable inert solvent such as 1,2-dichloroethane, benzene, ether, methylene chloride, toluene, chloroform, tetrahydrofuran, sulfolane, and the like. Although the reactants may be mixed together at or near room temperature or at elevated temperatures, and the vinyl chloroformate may be added to the tertiary amine, the preferred procedure for mixing the reactants, particularly in those reactions where HCl is lost on removal of the alkyl group (such as in the splitting off of some tertiary and secondary alkyl groups), is to add the tertiary amine slowly to a stoichiometric excess of the vinyl chloroformate in the cooled reaction solvent. The generally preferred addition temperature is in the range of −40° C. to 0° C., after which the mixture is allowed to warm to room temperature and then either left at room temperature for several hours or else heated for a shorter period. A short reflux period (for example, 30 minutes to an hour in 1,2-dichloroethane, often longer in benzene or ether) is often advantageous to eliminate a volatile alkyl halide if such is produced on dealkylation or to guarantee completion of the reaction when the dealkylation has not previously been attempted and its rate is unknown.

In the demethylation of complex and expensive tertiary amines, it is often commercially advantageous to perform the vinyl chloroformate addition at or above room temperature and to heat the reaction mixture at 60°–80° C. for several hours before work-up.

When HCl or other acid is liberated during the N-dealkylation, a suitable proton scavenger may advantageously be included in the reaction mixture to remove the acid. The proton scavenger may itself be a tertiary amine provided such is more basic but less reactive toward vinyl chloroformate than the amine to be dealkylated. Proton scavengers of this type which have been discovered to be particularly useful include 1,8-bis-(dimethylamino)-naphthalene, N-alkyldicyclohexylamines (such as N-methyl- or N-ethyldicyclohexylamines) and N-alkyl-2,2,6,6-tetramethylpiperidines. The former and the final series of proton scavengers above can be recovered in essentially quantitative yield after treatment with vinyl chloroformate in 1,2-dichloroethane at reflux for four hours. In N-dealkylation of tertiary amines with vinyl chloroformate, the inclusion of small amounts of proton scavengers like 1,8-bis-(dimethylamino)-naphthalene in the reaction mixture to tie up traces of acid impurities (generated for example from trace moisture) is often advantageous. If a stoichiometric amount of 1,8-bis-(dimethylamino)-naphthalene or a similar proton scavenger is included in the reaction medium for tertiary amino N-dealkylation with vinyl chloroformate, the tertiary amino hydrohalide or other acid salt may be used as the reactant without prior conversion to the free tertiary amine. This procedure is especially convenient when the tertiary amine to be N-dealkylated is most easily obtained or handled as some acid salt.

Reaction of vinyl chloroformate with a candidate tertiary amine having at least one alkyl group attached to the amino N atom results in the removal of the N-alkyl group or one of the N-alkyl groups from the amino N atom of the tertiary amine, and replacement thereof by the vinyloxycarbonyl or, as designated hereinbelow, the VOC group. The resulting VOC-amide of a secondary amine is thereafter cleaved to remove therefrom the VOC group and obtain the corresponding secondary amine as its hydrohalide or other acid salt.

Several techniques are available for removal of the VOC group from the amino N atom. For example, the VOC group may be split off by titration of the VOC-amide with bromine in an inert solvent followed by the addition of a volatile alcohol such as methanol or ethanol (ROH) and removal of the solvent, excess alcohol, and the BrCH$_2$CH(OR)$_2$ at reduced pressure to produce the secondary amine hydrobromide.

In another procedure the alcohol is present in solution with the VOC-amide as the bromine is added. Alternatively, the VOC group may be split off by treatment with 1.1 to 5 or more stoichiometric equivalents of an acid such as HCl or HBr in the presence of a hydroxylic reagent, such as water, a carboxylic acid or preferably an alcohol, which also often functions as the solvent. When other groups in a particular VOC-amide are sensitive to alcoholic acid, this cleavage may preferably be carried out as two separate steps. First, the VOC-amide is treated with HX (for example, HCl or HBr) in an inert solvent such as an ether or chlorinated hydrocarbon. Then the intermediate

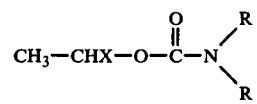

is freed from most excess acid and finally warmed with a volatile alcohol such as methanol or ethanol (ROH) yielding the secondary amine hydrohalide, CO$_2$, and CH$_3$CH(OR)$_2$. Solvent, byproducts, and excess reagents are easily removed by evaporation at reduced pressure. Moreover, the VOC group may be split off from the VOC-amide by mercuric ion induced hydrolysis with mercuric acetate in acetic acid.

Where the N-dealkylating agent is a group giving rise to the halo or polyhaloalkoxy carbonyl moiety, for example the 2,2,2-trichloroethoxy carbonyl group (TOC) the 14-acyloxy-N-TOC compound is dissolved in a lower alkanol or lower alkanoic acid or combination thereof, suitably in the presence of water, for example in aqueous acetic acid and treated with an electron donor, suitably metallic zinc.

The thus obtained acid salts of 14-acyloxymorphinans (4) are then further reacted in accordance with the ultimate intention of the synthetic sequence. Thus, where it is desired to form the corresponding 14-hydroxy unsubstituted secondary amino compound (5), for example, noroxymorphone in the naloxone synthesis and noroxycodone in the naltrexone synthesis, the salts (4) are treated with aqueous mineral acid under moderately vigorous conditions. It is preferred to take up the acid salt (4) in moderately strong aqueous mineral acid. An aqueous solution containing between about 15 and about 50% by weight of acid is suitable, sulfuric or hydrochloric acids being especially preferred. Suitably, there are utilized about 1 part by weight of the 14-acyloxy compound (4) to 10 parts by weight of acid. This ratio is in no way considered to be limiting; however, an excess of acid is desirable. For the best results, the hydrolysis is carried out in an inert atmosphere, suitably in a nitrogen atmosphere, under reflux. The reaction may run from between about two to about twenty hours, reaction times of between five and ten hours are generally preferred. The reaction mixture is then cooled, suitably to ice bath temperatures, and basified to a pH of between 8 and 10, suitably between 8.5 and 9.0, by addition of aqueous base, suitably concentrated ammonium hydroxide. Under certain circumstances, it is desirable to permit the solution to warm to ambient temperature (15° to 25° C.), acidify to about pH 2 to about pH 3 followed by extraction with a substantially water immiscible strong polar organic solvent, suitably a halogenated hydrocarbon such as chloroform. The organic extract is discarded and the aqueous solution rebasified as set forth hereinabove. In certain cases, for example, where the product is noroxymorphone, the addition of the base forms a precipitate which is effectively insoluble in common organic solvents. In this case, the precipitate is merely separated by filtration, washed with cold, suitably ice water, and dried under reduced pressure. In other cases, the basified solution is extracted with a strong polar substantially water immiscible solvent such as a halogenated hydrocarbon, suitably chloroform or methylene chloride. The organic extract is then dried, the solvent removed, and theresidue purified, suitably by passing through a short alumina column in the same or other polar substantially water-immiscible solvent.

Where the ultimately desired product is one wherein the realkylation of the ring nitrogen does not operate with high efficiency, for example the nalbuphine synthesis, the 14-acyloxy group originally chosen, for example cyclobutylcarbonyl, is caused to rearrange from a 14-O-acyl compound to an N-acyl compound by treatment of (4) with base, suitably mild base, followed by reduction of the carbonyl group to the corresponding methylene group. Where the starting compound (4) carries a keto moiety at the 6 position, this must, of course, be protected prior to the reduction step or else reoxidized if converted to the 6-alcohol during reduction. These procedures are set forth in greater detail in Applicants' co-pending application filed concurrently herewith.

As stated hereinabove, the conversion of the compound (5) formed in the manner set forth above to the desired N-substituted compound (6) is achieved by methods which will vary in accordance with the total structure of the compound, and the group which it is desired to place as a tertiary substituent upon the ring nitrogen. Thus, for example, where it is desired to form naloxone (7a) or other N-allyl analogs thereof having a 3,14-dihydroxy substitution pattern, compound (5) for example, noroxymorphone (5a), is allylated in the usual manner by reaction with allyl bromide in the presence of an acid scavenger, for example, sodium bicarbonate in an alkanolic medium, suitably absolute ethanol under an inert atmosphere, for example, a nitrogen atmosphere, by heating under reflux for between fifty and seventy hours. Despite the occurrence of phenol allylation which accounts for some yield loss, it has been found satisfactory to proceed in this direct manner.

On the other hand, where it is desired to prepare naltrexone (7b), it was found desirable to proceed via N-cyclopropylmethylnoroxycodone (6b) where this problem does not arise since the phenolic hydroxy at the 3-position is methylated. Thus, it is possible to force the cyclopropylmethylation at the nitrogen which will give substantially better yield of the end product than it was heretofore available. Under the methods of the art, it was customary to alkylate — i.e., cyclopropylmethylate — noroxymorphone which was not as efficient a process as desired due to the cyclopropylmethylation of the phenolic hydroxy group.

The N-cyclopropylmethylnoroxycodone (6b) is then O-demethylated, suitably by the high temperature pyridine hydrochloride method or one of the other methods used in the art, (e.g. $BBr_3$) for the conversion of oxycodone to oxymorphone.

It has been our surprising finding that making naltrexone via noroxycodone and N-cyclopropylmethylnoroxycodone is more efficient (circa 54% overall from oxycodone) than proceeding via noroxymorphone to naltrexone even when produced by the novel procedures of the present invention (43% overall from oxycodone via oxymorphone). Both procedures are more than twice as efficient as the procedures of the art which produce noroxymorphone from oxycodone via oxymorphone (Seki, Takamine Kenkyusho Nempo, 12, 56 (1960)), which proceed in an overall yield of about 21%. A third procedure for the synthesis of naltrexone is set forth in Applicant's co-pending application filed concurrently herewith.

Where it is desired to form the other compounds within the scope of the present invention wherein the N-substituent is other than methyl, the ether bridge between positions 3 and 5 has been replaced by hydrogen substituents, and the group at position 6 is either oxo or two hydrogen atoms one may proceed by either the route set forth for the synthesis of naloxone or the route set forth for the synthesis of naltrexone.

The foregoing discussions and the following experimental examples should be considered merely as illustrative of the invention and in no way limiting thereof. In the following Examples, all temperatures are in ° C. Silica Gel $GF_{254}$ plates with 90% methylene chloride — 10% methanol (v/v) as the eluent were used for tlc analyses to obtain the $R_f$ reference values.

EXAMPLE I

3,14-DIACETYLOXYMORPHONE (2a)

Oxymorphone (1a) (3.01 g, 0.01 mole) in 25 ml of acetic anhydride was heated under nitrogen with stirring for two hours at 100° C. The volatiles were then removed in vacuo and the product was vacuum dried (0.2 torr) for two days to yield 3,14-diacetyloxymorphone (2a) as an off-white powder; mp 215°–219° C. (Lit.: Lewenstein residue (Brit. Pat. No. 955,493) (1964) mp 220° C., Seki residue (Takamine Kenkyusho Nempo, 12, 56 (1960) mp 209°–213° C., Seki ethanol recrystalized mp 214°–215° C.); yield 3.90 g (100%); tlc: single spot of $R_f$0.51. Although the compound could be recrystallized from ethanol (with significant loss by hydrolysis), its purity as determined by NMR analysis and tlc made this purification step superfluous.

IR($\mu$): 3.54 (w), 3.60 (m), 3.63 (w), 5.69 (s), 5.75 (sh), 5.79 (s), 6.15 (m); $CH_2Cl_2$.

NMR($\delta$): 6.9-6.5 (m), 4.62 (s), 4.3-4.1 (m), 3.5-1.2 (m), with large spikes of equal area at 2.32, 2.29, and 2.16; ratio 2:1:1:19; $CDCl_3$.

MS(m/e): 385.1543 (P, 18%, Calc. 385.1524), 343.1428 (P-$CH_2CO$, 68%, Calc. 343.1419), 284 (33%), 43 (100%)

In accordance with the above procedures but starting in place of oxymorphone (1a) with N-methyl-3,14-dihydroxymorphinan (1e) or N-methyl-3,14-dihydroxy-6-oxomorphinan (1f) there is obtained N-methyl-3,14-diacetoxymorphinan (2e) or N-methyl-3,14-diacetoxy-6-oxomorphinan (2f).

EXAMPLE II

14-ACETYLOXYCODONE (2b)

(Method of Freund and Speyer, J. Prakt Chem. 94, 135 (1916)).

Oxycodone (1b) (15.8 g, 0.05 mole) was refluxed in freshly distilled acetic anhydride (75 ml) (Baker) for 45 minutes. After cooling, the solution was poured onto ice (300 g) and stirred while allowed to warm to room temperature to hydrolyze residual anhydride. The solution was again cooled to ca. 15° C. and then kept at this temperature while cold concentrated aqueous ammonium hydroxide was added to raise the pH to 9 and precipitate the product. The mixture was further cooled to 0° C. before the product was filtered off, washed with cold water (75 ml), and vacuum dried; 14-acetyloxycodone (2b) is given as white powder of mp 207°-213° C.; yield 17.9 g (100%); tlc: single spot of $R_f$ 0.50 (the $R_f$ of oxycodone in this system was 0.46). Recrystallization from 95% ethanol gave pure white needles; mp 213°-215° C. (Lit. Freund and Speyer 215°-216° C.).

IR($\mu$): 3.53 (w), 3.57 (w), 3.59 (w), 5.74 (sh), 5.79 (s), 6.11 (w), 6.21 (w); $CH_2Cl_2$.

NMR($\delta$): 6.9-6.5 (m), 4.69 (s), 4.3-4.1 (m), 3.94 (s), 3.5-1.2 (m, with large spikes at 2.36 and 2.20); ratio 2:1:1:3:16; $CDCl_3$.

MS(m/e): 357 (P, 100%), 314 (P-Ac, 52%).

Only 89% of the product was recovered from the recrystalization: thus, the white powdered reaction product was ordinarily used in subsequent reactions.

EXAMPLE III

14-CYCLOBUTYLCARBONYLOXYCODONE (2c)

A solution of oxycodone (1b) (7.88 g, 0.025 mole) and cyclobutanecarboxylic acid anhydride (9.11 g, 0.05 mole) in dry dioxane (30 ml) was heated (under nitrogen) at 100° C. for 18 hours. After cooling, the solvent was removed at reduced pressure and the residue, an orange oil, was diluted with water (100 ml). Aqueous 20% hydrochloric acid (3 ml) was added to dissolve the amine and the mixture was stirred for two hours to hydrolyze the remaining anhydride. The solution was then cooled (ice bath) and taken to ca. pH 11 with cold concentrated aqueous ammonium hydroxide. Next, the precipitated product was filtered off, washed with cold water (50 ml), and vacuum dried; pale yellow grannular solid; mp 140.5°-144.5° C.; yield 9.93 g (100%); tlc: single spot of $R_f$ 0.60.

Recrystalization from ethanol gave 14-cyclobutylcarbonyloxycodone (2c) as fine white needles; mp 149.7°-150.3° C.; analysis sample mp 150.9°-151.1° C.

Only 78% of the product was recovered from the ethanol recrystalization steps; thus, the recrystalization was omitted in the preparation of material for use in the following N-demethylation reaction.

Calc. for $C_{23}H_{27}NO_5$: C, 69.50%; H, 6.85%; N, 3.52%; Found: C, 69.41%; H, 6.81%; N, 3.66%.

IR($\mu$): 3.56 (w), 3.60 (m), 3.64 (w), 5.73-5.91 (s), 6.12 (w), 6.21 (m): $CH_2Cl_2$.

NMR($\delta$): 6.8-6.5 (m), 4.63 (s), 4.3-4.1 (m), 3.87 (s), 3.5-1.2 (m, with large spike at 2.31); ratio 2:1:1:3:20; $CDCl_3$.

MS(m/e): 397.1875 (P, 100%, Calc. 397.1889), 314.1392 (P-cyclobutylcarbonyl, 51%, Calc. 314.1392), 298 (18%), 55 (27%).

In accordance with the above procedure but where in place of oxycodone there is used as starting material 3-propyloxymorphone, 3-cyclopropyloxymorphone, 3-cyclopentyloxymorphone, 3-ethoxy-14-hydroxy-6-oxomorphinan and the like, there is obtained the corresponding 3-propyl-14-acetyloxy morphone, 3-cyclopropyl-14-acetyloxymorphone, 3-cyclopentyl-14-acetyloxymorphone, 3-ethoxy-14-acetyloxy-6-oxo-morphinan and the like.

EXAMPLE IV

CYCLOBUTANECARBOXYLIC ACID ANHYDRIDE

Cyclobutanecarboxylic acid (Aldrich) (24.0 g, 0.24 mole) in 25 ml of ether was added (10 minutes) to a cooled, mechanically stirred solution of pyridine (Fisher) (18.9 g, 0.24 mole) in ether (200 ml). After 15 minutes, the ice bath was replaced by an ice-salt bath (−8° C.) and cyclobutanecarboxylic acid chloride (Aldrich) (28.4 g, 0.24 mole) in 25 ml of ether was slowly added (45 minutes) with vigorous stirring. During the addition, another 50 ml of ether was added to facilitate the stirring of the mixture as it thickened with precipitated pyridine hydrochloride. The cooling bath then was removed and the mixture was stirred for another hour. After removal of the amine salt by filtration, the product was isolated from the filtrate by vacuum distillation; bp 77°-79° C. at 0.6 torr (Lit. Freund and Gudeman, Chem. Ber. 21, 2692, (1888) 160° C.) yield 37.9 g (88%).

IR($\mu$): 5.51 (s), 5.73 (s); $CCl_4$.

NMR($\delta$): 3.5-2.9 (m), 2.6-1.6 (m); ratio 2:12; $CCl_4$.

EXAMPLE V

N-VOC-3,14-DIACETYLNOROXYMORPHONE (3a)

A flask containing unpurified 3,14-diacetyloxymorphone (2a) (3.90 g, 0.01 mole) was evacuated for three hours (0.3 torr) in a 90° C. oil bath. After the oil bath had cooled to 65° C., the vacuum was replaced by a dry nitrogen atmosphere and 1,2-dichloroethane (15 ml) was added to the flask. Next, vinyl chloroformate (0.03 mole) was syringed into the stirred, pale yellow solution. After 23 hours at 65° C. and one hour at reflux, the volatiles were removed and the residue, a pale yellow foam, was vacuum dried. The foam was then dissolved in ethyl acetate (100 ml) and washed with 0.3 N hydrochloric acid (30 ml), water (30 ml), aqueous 1% sodium bicarbonate (30 ml), and water (30 ml). The dried (over sodium sulfate) solution was evaporated at reduced pressure affording an off-white foam of N-VOC-3,14-diacetylnoroxymorphone (3a); yield 4.44 g (100%); tlc: single spot of $R_f$ 0.74. This material was not further purified but taken on directly to noroxymorphone (5a) as described in the following Example.

An analysis sample was prepared by eluting a chloroform solution of reaction product through a short silica gel 60 column followed by evaporation of the total eluate and recrystalization (twice) from methylene chloride pentane: mp 210.5°-211.5° C.

Calc. for $C_{23}H_{23}NO_8$: C, 62.58%; H, 5.25%; N, 3.17%. Found: 62.89%; H, 5.15%; N, 3.37%.

IR($\mu$): 5.66 (s), 5.73 (s), 5.81 (sh), 5.85 (s), 6.08 (m), 6.18 (w); $CH_2Cl_2$.

NMR($\delta$): 7.4-6.5 (m), 5.7-5.4 (broad), 5.1-1.3 (m, with small spike at 4.65 and two large spikes of equal area at 2.28 and 2.10); ratio 3:1:19; $CDCl_3$.

MS(m/e): 441.1452 (P, 3%, Calc. 441.1422), 398.1238 (P-acetyl), 10%, Calc. 398.1239), 339 (27%), 314 (8%), 312 (10%), 296 (14%), 270 (10%), 43 (100%).

Starting 3,14-diacetyloxymorphone (3a) was recovered from the pooled aqueous wash solutions from the first experiment above by basification (with sodium carbonate) and extraction into chloroform (3 × 30 ml). After washing with water (30 ml) the dried (over sodium sulfate) extract was evaporated to an off-white solid; yield 0.12 g (3%); tlc: one spot of $R_f$ 0.51 (starting material) plus a trace at $R_f$ 0.47 (monoacetyl compound).

EXAMPLE VI

N-VOC-14-ACETYLNOROXYCODONE (3b)

A flask containing 14-acetyloxycodone (2b) (7.15 g, 0.02 mole) was evacuated for one hour (0.2 torr) in a 65° C. oil bath. After substitution of a dry nitrogen atmosphere for the vacuum, dry 1,2-dichloroethane (20 ml) was added to the cooled flask (ice bath). Next, vinyl chloroformate (0.06) mole in 1,2-dichloroethane (10 ml) was dripped into the stirred white suspension (10 minutes). During the next hour, the mixture was gradually warmed up to 65° C. and then left at that temperature for 23 hours. An hour's reflux preceded rotary evaporation of the volatiles. The residue, a white foam, was partitioned between water (50 ml) and 4:1 ethyl acetate-ether (125 ml). The aqueous layer was separated and the organic layer then washed with 0.3 N hydrochloric acid (2 × 20 ml), 0.1 N hydrochloric acid (20 ml), water (20 ml), aqueous 1% sodium bicarbonate (20 ml), and water (20 ml). Back extraction of the combined aqueous washes with fresh ethyl acetate (50 ml) preceded drying over anhydrous sodium sulfate and vacuum evaporation which gave a white granular solid; mp 181°–182.5° C.; yield 7.73 g (94%); tlc: single spot of $R_f$ 0.64. Recrystalization from methanol or methylene chloride-pentane afforded N-VOC-14-acetyloxycodone (3b), mp 182.5°–183.5° C.

Calc. for $C_{22}H_{23}NO_7$: C, 63.92%; H, 5.61%, N, 3.39%. Found: C, 63.76%, H, 5.83%; N, 3.47%.

IR($\mu$): 3.50 (w), 5.73 (s), 5.78 (s), 5.84 (s), 6.07 (m), 6.14 (w); $CH_2Cl_2$.

NMR($\delta$): 7.4-7.0 (m), 6.9-6.6 (m), 5.7-5.5 (broad), 5.1-3.8 (m, with small spike at 4.68 and large spike at 3.89), 3.4-1.3 (m, with large spike at 2.12); ratio 1:2:1:7:12; $CDCl_3$.

MS(m/e): 413.1466 (P, 73%, Calc. 413.1473), 354.1324 (P-OAc, 28%, Calc. 354.1340), 353.1266 (P-HOAc, 100%, Calc. 353.1262), 328 (47%), 326 (54%), 310 (94%), 284 (81%).

The aqueous solution from the above extractions was made basic with sodium carbonate and then extracted with chloroform (3 × 50 ml). The unreacted 14-acetyloxycodone was recovered as a white solid by evaporation of this dried over sodium sulfate solution. White needles were obtained by recrystalization from 95% ethanol; mp 212°–214° C. (lit. 215°–216° C.); yield 0.3 g (4%).

In accordance with the above procedure but where in place of 14-acetyloxycodone, there is utilized N-methyl-3,14-diacetoxymorphinan (2e) or N-methyl-3,14-diacetoxy-6-oxomorphinan (2f), there is obtained the corresponding N-VOC-3,14-diacetoxymorphinan (3e) and N-VOC-3,14-diacetoxy-6-oxomorphinan (3f).

Similarly, but where in place of vinyl chloroformate there is used 2,2,2-trichloroethyl chloroformate, or phenyl chloroformate, there are obtained the corresponding N-TOC-(i.e., N-trichloroethoxycarbonyl) or N-POC-(i.e., N-phenoxycarbonyl) compounds, respectively.

EXAMPLE VII

N-VOC-14-CYCLOBUTYLCARBONYLNOROXYCODONE (3c)

A reaction flask containing 14-cyclobutylcarbonyloxycodone (2c) (5.96 g, 0.15 mole) prepared in accordance with Example III was evacuated for an hour at 0.4 torr in an 80° C. oil bath. Next, the vacuum was replaced by a dry nitrogen atmosphere, and when the oil bath had cooled to 63° C., dry 1,2-dichloroethane (20 ml) was syringed into the flask. Vinyl chloroformate (0.045 mole) in 1,2-dichloroethane (5 ml) was then dripped into the stirred homogeneous reaction mixture (10 minutes). After 23 hours at this temperature, the mixture was refluxed for an hour and the volatiles were then removed at reduced pressure. The off-white foamy residue was next partitioned between 4:1 ethyl acetate-ether (100 ml) and water (20 ml). After separation, the organic layer was washed with 0.3 N hydrochloric acid (20 ml), water (20 ml), aqueous 1% sodium bicarbonate (20 ml), and water (20 ml), then dried over sodium sulfate and evaporated in vacuo, to yield N-VOC-14-cyclobutylcarbonylnoroxycodone (3c) as a white foam (6.42 g, 94%) which could not be crystalized; its spectral properties and behavior in subseqent reactions indicated the presence of only one compound; tlc: single spot of $R_f$ 0.74. A sample was prepared for combustion analysis by eluting a chloroform solution of the compound through a short silica gel 60 column followed by vacuum evaporation of the total eluate and vacuum drying of the glass at 70° C.

Calc. for $C_{25}H_{27}NO_7$: C, 66.21%; H, 6.00%; N, 3.09%. Found: C, 66.15%; H, 6.21%; N, 2.86%.

IR($\mu$): 3.56 (w), 5.71-5.92 (s), 6.08 (m), 6.12 (sh), 6.22 (w); $CH_2Cl_2$.

NMR($\delta$): 7.4-7.0 (m), 6.9-6.5 (m), 5.8-5.5 (broad), 5.1-3.7 (m, with small spike at 4.68 and large spike at 3.92), 3.5-1.3 (m); ratio 1:2:1:7:16; $CDCl_3$.

MS(m/e): 453.1763 (P, 78%, Calc. 453.1785), 366 (44%), 353.1224 (P-cyclobutanecarboxylic acid, 100%, Calc. 353.1262), 310.1054 (P-cyclobutanecarboxylic acid-vinyloxy, 58%, Calc. 310.1078), 284 (53%), 254 (25%), 240 (32%), 226 (24%), 212 (37%).

Unreacted 14-cyclobutylcarbonyloxycodone (2c) was recovered by basification (solid sodium carbonate) and chloroform extraction of the combined aqueous washes. The tan solid obtained after drying over sodium sulfate and evaporation of the extract was recrystalized from 95% ethanol; off-white needles of mp 148.5°–149.5° C.; yield 0.30 g (5%).

EXAMPLE VIII

N-(2,2,2-TRICHLOROETHOXYCARBONYL)-14-CYCLOBUTYLCARBONYLNOROXYCODONE (3d)

A flask containing 14-cyclobutylcarbonyloxycodone prepared in accordance with Example III (1.19 g, 0.003 mole) was immersed in a 90° C. oil bath and evacuated (0.3 torr) for two hours. The vacuum was replaced by a dry nitrogen atmosphere and when the oil bath had cooled to 65° C., 1,2-dichloroethane (8 ml) was syringed into the flask. Next 2,2,2-trichloroethyl chloroformate (Aldrich, stored over potassium carbonate) (1.27 g, 0.006 mole) in 1,2-dichloroethane (2 ml) was added (10 minutes). After 23 hours at 65° C. and one hour at reflux, the volatiles were removed and the red oily residue was evacuated overnight. It was then dissolved in ethyl acetate (50 ml) and washed with 0.3 N hydrochloric acid (15 ml), water (15 ml), aqueous 5% sodium bicarbonate (15 ml), and water (15 ml). The organic layer dried over sodium sulfate was evaporated to a light brown foam which was taken up in chloroform (5 ml)

and eluted through a short silica gel 60 column (chloroform as eluant) to remove the color. Evaporation of the total eluate afforded N-2,2,2-trichloroethoxycarbonyl-14-cyclobutylcarbonylnoroxycodone (3d) as a substantially pure white foam which was kept at 0.3 torr for two days at 60° C.; tlc: single spot of $R_f$ 0.68. From NMR and IR analysis, the product (1.40 g) was estimated to contain ca. 6% 2,2,2-trichloroethyl chloroformate as a contaminant; corrected estimated product yield 79%. Since the contaminant did not interfere in the next reaction, further purification of this material was not attempted.

IR($\mu$): 5.75 (sh), 5.77 (s), 5.84 (s), 6.11 (w); $CH_2Cl_2$; 2,2,2-trichloroethyl chloroformate at 5.61 (w).

NMR($\delta$): 6.9-6.5 (m), 5.9-5.4 (broad), 5.1-1.3 (m, with small spike at 4.82, medium spike at 4.66, and large spike at 3.85); ratio 2:1:23; $CDCl_3$; 2,2,2-trichloroethyl chloroformate at 4.89.

MS(m/e): 559.0746 (P, 12%, Calc. 559.0745), 557.0726 (P, 13%, Calc. 557.0774), 459 (45%), 457 (46%), 366 (5%), 326 (5%), 284 (9%), 240 (13%), 211 (16%), 133 (14%), 131 (14%), 84 (23%), 55 (100%), 35 (18%).

The aqueous wash solutions were combined, basified with sodium carbonate, and extracted with methylene chloride (4 × 15 ml). The extract was washed with water (20 ml), dried over sodium sulfate, and evaporated to a reddish solid residue. By recrystalization from 95% ethanol, unreacted 14-cyclobutylcarbonyloxycodone (3d) was recovered as white needles; mp 148.5°-149.5° C.; yield 0.23 g (19%).

In a similar N-demethylation reaction carried out for 65 hours at 70° C. and five hours at reflux, the estimated yield of product was 73% and only 10% of the starting material was recovered.

Unpurified N-[2,2,2-trichloroethoxycarbonyl]-14-cyclobutylcarbonylnoroxycodone (9'b) (1.36 g. containing ca. 10% 2,2,2-trichloroethyl chloroformate) (0.0022 mole) was dissolved in aqueous 90% acetic acid (45 ml). Zinc dust (Fisher) (1.44 g, 0.022 mole) was added in six portions at 10 minute intervals and the mixture then was stirred for three hours. After filtration, the filtrate was taken to dryness at reduced pressure (25° C., 1 Torr) to yield, 14-cyclobutylcarbonylnoroxycodone acetic acid salt in the presence of zinc acetate and zinc chloride. These inorganic contaminents are generally not removed as they do not interfere with subsequent stages of the reaction sequence.

The NMR spectrum of the above material was found to be substantially identical (except for excess acetate absorption from zinc acetate) to the spectrum of material derived from 14-cyclobutylcarbonylnoroxycodone hydrochloride (from Example II).

EXAMPLE IX

3,14-DIACETYLNOROXYMORPHONE HYDROCHLORIDE (4a) AND NOROXYMORPHONE (5a)

Hydrogen chloride (Matheson, technical, passed through calcium chloride) was bubbled through a stirred solution of the foamy N-VOC-3,14-diacetylnoroxymorphone (3a) (4.44 g), in methylene chloride (60 ml) at ca. 20 cc per minute for 75 minutes. The solvent was removed in vacuo and the leftover pale yellow foam (the hydrogen chloride adduct) was heated under nitrogen at 55° C. for 45 minutes in 60 ml of absolute methanol. Evaporation of the volatiles gave 3,14-diacetylnoroxymorphone hydrochloride (4a) as a pale yellow foam which was dried overnight at 0.3 torr.

IR($\mu$): 3.5-4.1 (m, broad), 5.67 (s), 5.72 (sh), 5.74 (s): $CH_2Cl_2$.

NMR($\delta$): 10.9-9.0 (very broad), 7.1-6.6 (m), 5.2-4.5 (broad, with small spike at 4.74), 4.2-1.2 (m, with two large spikes at 2.44 and 2.30); ratio 2:2:2:16; $CDCl_3$.

In accordance with the above procedures but where in place of N-VOC-3,14-diacetylnoroxymorphone there is utilized N-VOC-3,14-diacetoxymorphinan (3e) or N-VOC-3,14-diacetoxy-6-oxomorphinan (3f), there is obtained 3,14-diacetoxymorphinan hydrochloride (4e) and 3,14-diacetoxy-6-oxo-morphinan hydrochloride (4f).

Subsequent reflux of 3,14-diacetylnoroxymorphone hydrochloride (4a) for five hours (reaction is not complete by tlc after 3.5 hours) in aqueous 25% sulfuric acid (45 ml) afforded the acid salt of noroxymorphone (5a) which was neutralized to give 5a and precipitated by taking the cooled (ice bath), stirred, burgundy reaction mixture to pH 8.8 (pH meter) with concentrated aqueous ammonium hydroxide. The filtered product was washed with ice water (30 ml) and dried in vacuo to yield noroxymorphone (5a) as a gray powder with no mp; darkened above 260° C.; complete char at 360° C. (lit.: Lewenstein supra no mp, lit.: Seki supra 310°-313° C.); yield 2.73 g (95% based on oxymorphone without subtraction of recovered 3,14-diacetyloxymorphone in preceding Example). Noroxymorphone (5a) is virtually insoluble in common organic solvents.

When the reaction sequence was performed on a smaller scale with recrystalized N-VOC-3,14-diacetylnoroxymorphone, the hydrolysis solution ended up pale yellow instead of burgundy and the noroxymorphone (5a) (95% yield, still no mp) was off-white in color.

IR($\mu$): 2.8-4 (s, broad), 5.84 (s), 6.15 (m); KBr.

MS(m/e): 287.1169 (P, 100%, Calc. 287.1157), 207 (61%).

In accordance with the above procedure, but where in place of 3,14-diacetylnoroxymorphone (4a) there is subjected to the acid hydrolysis 3,14-diacetoxymorphinan hydrochloride (4e) or 3,14-diacetoxy-6-oxomorphinan hydrochloride (4f) there are obtained the corresponding 3,14-dihydroxymorphinan (5e) and 3,14-dihydroxy-6-oxomorphinan (5f).

EXAMPLE X

14-ACETYLNOROXYCODONE HYDROCHLORIDE (4b)

Hydrogen chloride (Matheson, technical, passed through calcium chloride ) was bubbled through a stirred solution of N-VOC-14-acetylnoroxycodone (3b) (1.00 g, 0.0024 mole) in methylene chloride (20 ml) at a moderate rate (20 cc per minute) for 15 minutes and then slowly (5 cc per minute) for another 45 minutes. The solvent was evaporated in vacuo and the leftover white foam was heated at 50° C. for 30 minutes in absolute methanol (20 ml). Evaporation of the solvent at reduced pressure gave 14-acetylnoroxycodone hydrochloride (4b) as a white granular solid which was recrystallized from methanol ether; mp 214°-216° C. dec; yield 0.82 g (89%); analysis sample mp 215°-217° C. dec.

Calc. for $C_{19}H_{22}NO_5Cl$: C, 60.08%; H, 5.84%; N,, 3.69%; Cl, 9.33%. Found: C, 59.89%; H, 6.08%; N, 3.70%; Cl, 9.36%.

IR(μ): 3.56 (sh), 3.55-3.94 (m), 5.69-5.83 (s, 5.76 max.), 6.13 (w), 6.21 (w); CH$_2$Cl$_2$.

NMR(δ): 10.8-9.4 (very broad), 6.78 (s), 5.2-4.8 (broad), 4.74 (s), 3.91 (s), 3.7-1.4 (m, with large spike at 2.46); ratio 2:2:1:1:3:13; CDCl$_3$.

MS(m/e): 343.1451 (P-HCl, 100%, Calc. 343.1419), 300.1236 (P-HCl-Ac, 19%, Calc. 300.1235), 201 (22%), 43 (45%), 35 (20%).

EXAMPLE XI

14-CYCLOBUTYLCARBONYLNOROXYCODONE HYDROCHLORIDE (4c)

Hydrogen chloride (Matheson, technical, passed through calcium chloride) was bubbled (ca. 20 cc per minute) through a stirred solution of N-VOC-14-cyclobutylcarbonylnoroxycodone (3c) (2.72 g, 0.006 mole) prepared in accordance with Example VII in methylene chloride (40 ml) for 2.5 hours. The methylene chloride was removed in vacuo and the remaining white foam was refluxed for an hour in methanol (40 ml). Vacuum evaporation of the volatiles gave a white granular solid; mp 212.5°-213.5° C. dec; yield 2.52 g (100%). The reaction product was recrystalized from methanol-ether to further purify the 14-cyclobutylcarbonylnoroxycodone hydrochloride (4c), mp 214°-215° C. dec; yield 2.01 g (80%); second crop: mp 211.5°-212° C. dec; yield 0.09 g (4%); analysis sample mp 217° C. dec.

Calc. for C$_{22}$H$_{26}$NO$_5$Cl: C, 62.93%; H, 6.24%; N, 3.34%; Cl, 8.44%. Found: C, 63.11%; H, 6.49%; N, 3.39%; Cl, 8.58%.

IR(μ): 3.56 (sh), 3.54-3.99 (m), 5.73-5.82 (s, 5.77 max.), 6.13 (w), 6.22 (w); CH$_2$Cl$_2$.

NMR(δ): 10.6-9.4 (very broad), 6.77 (s), 5.2-4.9 (broad), 4.73 (s), 4.0-1.2 (m, with large spike at 3.91); ratio 2:2:1:1:20; CDCl$_3$.

MS(m/e): 383.1743 (P-HCl, 100%, Calc. 383.1732), 300 (43%), 277 (28%), 216 (28%), 212 (22%).

EXAMPLE XII

NOROXYCODONE (5b) FROM N-VOC-14-ACETYLNOROXYCODONE (3b) WITHOUT ISOLATION OF 14-ACETYLNOROXYCODONE HYDROCHLORIDE

Hydrogen chloride (Matheson, technical, passed through calcium chloride) was bubbled through a stirred solution of crude N-VOC-14-acetylnoroxycodone (3b) (11.88 g, 0.0287 mole) in methylene chloride (200 ml) for 100 minutes at a moderate rate (20 cc per minute). The solvent was removed in vacuo; and after overnight drying (0.3 torr), the off-white foam was gently refluxed for 30 minutes in 200 ml of absolute methanol. Evaporation of the solvent gave 14-acetylnoroxycodone hydrochloride (4b) as a white, granular solid which was dissolved in aqueous hydrochloric acid (225 ml) and heated for four hours at 100° C. The solution was cooled, basified with concentrated ammonium hydroxide, and allowed to warm to room temperature. Acidification of the solution to pH 2-3 with concentrated hydrochloric acid was followed by extraction with chloroform (3 × 50 ml). The aqueous solution was then rebasified with concentrated aqueous ammonium hydroxide and extracted with chloroform (9 × 75 ml). The dried (over sodium sulfate) extract was concentrated to a greenish-brown solid which was dissolved in chloroform (25 ml) and passed through a short basic alumina column (15 g, chloroform as eluant) where the reddish color was removed. Vacuum evaporation of the total eluate gave noroxycodone (5b) as off-white microneedles of mp 164°-166° C. foaming, then 305° C. dec (lit.: Seki supra, 160° C. foaming, then 310° C. dec); yield 7.09 g (82%); tlc: single spot of R$_f$0.06. The compound was not crystalized before use since previous published attempts to recrystalize it had failed. According to Seki(vide supra), the compound analyzes satisfactorily without further purification.

IR(μ): 2.96 (sh), 2.95-3.05 (w), 3.56 (w), 5.79 (s), 6.13 (w), 6.22 (m); CH$_2$Cl$_2$.

NMR(δ): 6.8-6.4 (m), 4.61 (s), 3.9-1.2 (m, with large spike at 3.87); ratio 2:1:16; CDCl$_3$.

Ms(m/e): 301 (P, 100%), 216 (52%), 201 (14%), 188 (26%), 175 (18%), 126 (22%), 115 (21%).

EXAMPLE XIII

CYCLOPROPYLCARBINYL BROMIDE

This compound was prepared from cyclopropyl carbinol (Aldrich) and phosphorous tribromide (Baker) according to Meek (J.A.C.S. 77 6675 (1955)); bp 108.5°-110° C. (lit. 101.5°-102° C. at 627 torr).

NMR (δ): 3.30 (d, J=7), 1.6-0.2 (m); ratio 2:5; CCl$_4$.

EXAMPLE XIV

N-CYCLOPROPYLMETHYLNOROXYCODONE (6b)

A suspension of noroxycodone (5b) (6.03 g, 0.02 mole), cyclopropylcarbinyl bromide (8.10 g, 0.06 mole), and sodium carbonate (3.18 g, 0.03 mole) in 120 ml of 1:1 95% ethanol/chloroform was stirred (under nitrogen) at 60° C. for 3.5 days. Volatiles were evaporated and the remaining solid was partitioned between chloroform (150 ml) and water (150 ml). After separation, the aqueous layer was extracted with more chloroform (2 × 100 ml). The total extract was washed with water (100 ml), dried over sodium sulfate, and concentrated to ca. 25 ml which was then passed through a short silica gel 60 column (hot chloroform as eluant) where most of the brown color was removed. Evaporation of the total eluate gave a pale yellow foam identified as N-cyclopropylmethylnoroxycodone (6b) which crystallized from ether/pentane to give white "angel hair" crystals of mp 98.4°-99.1° C.; yield 5.85 g (82%); tlc: single spot of R$_f$0.54 versus R$_f$0.06 for noroxycodone. By concentration of the filtrate, a second crop of off-white crystals was obtained; mp 97.3°-98° C.; yield 0.32 g (5%); tlc: single spot of R$_f$0.54; analysis sample mp 99.1°-99.3° C. Though the last filtrate residue (0.31 g) was mostly product, a less polar contaminant (R$_f$ 0.76) was also present.

Calc. for C$_{21}$H$_{25}$NO$_4$: C, 70.96%; H, 7.09%; N, 3.94%. Found: C, 70.75%; H, 7.29%; N, 4.05%.

IR(μ): 2.94-3.07 (w), 3.58 (m), 5.78 (s), 6.11 (w), 6.22 (m); CH$_2$Cl$_2$.

NMR(δ): 6.8-6.4 (m), 4.7-4.3 (broad, with small spike at 4.63), 3.89 (s), 3.4-0.0 (m); ratio 2:2:3:18; CDCl$_3$.

MS(m/e): 355.1776 (P, 100%, Calc. 355.1784), 314.1390 (P-cyclopropyl, 22%, Calc. 314.1392), 110 (19%), 55 (50%).

In accordance with the above procedure, but where in place of noroxycodone (5b) there is utilized 3,14-dihydroxy-6-oxomorphinan (5f) there is obtained N-cyclopropylmethyl-3,14-dihydroxy-6-oxomorphinan (7f).

EXAMPLE XV

N-ALLYLNOROXYCODONE (6g)

Noroxycodone (5b) (7.13 g, 0.0237 mole), allyl bromide (Aldrich, redistilled) (5.72 g, 0.0473 mole), and sodium bicarbonate (3.98 g, 0.0473 mole) in 200 ml of 1:1 ethanol-chloroform was heated with stirring (under nitrogen) for 5 days at 60° C. After evaporation of the volatiles, a white residue remained. This was partitioned between water (50 ml) and chloroform (150 ml), and after separation, the aqueous layer was extracted with more chloroform (2 × 30 ml). Then the total chloroform solution was washed with water (50 ml), dried over sodium sulfate, and concentrated to an off-white solid. This was recrystalized from ethanol to yield N-allylnoroxycodone (6g) as white oblong crystals of mp 137°–137.5° C. (lit. Sankyo.Belg.Pat. No. 615,009 (1962) 132°–134° C.); yield 7.08 g (88%); tlc: single spot of $R_f$ 0.61, the $R_f$ of noroxycodone was 0.06; analysis sample mp 137.2°–137.9° C.

Calc. for $C_{20}H_{23}NO_4$: C, 70.36%; H, 6.79%; N, 4.10%. Found: C, 69.94%; H, 6.92%; N, 4.05%.

IR($\mu$): 2.94–3.08 (w), 3.57 (m), 5.79 (s), 6.14 (w), 6.22 (m); $CH_2Cl_2$.

NMR($\delta$): 6.8–6.4 (m), 6.1–5.5 (m), 5.4–4.5 (m, with small spike at 4.61), 3.87 (s), 3.3–1.3 (m); ratio 2:1:4:3:13; $CDCl_3$.

MS(m/e): 341.1614 (P, 100%, Calc. 341.1626), 300.1268 (P-allyl, 12%, Calc. 300.1235), 256 (18%), 96 (15%), 70 (15%), 41 (30%).

EXAMPLE XVI

NALOXONE (7a) FROM NOROXYMORPHONE (5a)

A suspension of noroxymorphone (5a) (2.73 g, 0.0095 mole), allyl bromide (Aldrich, redistilled) (1.26 g, 0.0104 mole), and sodium bicarbonate (Fisher) (1.20 g, 0.0143 mole) in 200 ml of absolute ethanol was heated (under nitrogen) with stirring for 60 hours at 70° C. The volatiles then were removed in vacuo and the remaining brown solid was dissolved in hydrochloric acid (50 ml, 0.5 N). The solution was filtered to remove a brown flocculence, extracted with chloroform (2 × 20 ml), refiltered, and taken to pH 13.5 (pH meter) with aqueous potassium hydroxide (30%). In order to remove any O-allyl product, this solution was extracted with chloroform (3 × 40 ml). After another filtration to remove a trace flocculence, the pH of the solution was lowered to 8.8 (pH meter) with aqueous hydrochloric acid (20%) and the desired N-allylnoroxymorphone (7a) was extracted into chloroform (8 × 50 ml). The total extract was washed with water (75 ml), dried over sodium sulfate (anhydrous), and concentrated to ca. 25 ml. This dark brown solution was passed through a short silica gel 60 column (hot chloroform as eluant) where all of the brown color was removed. Evaporation of the total eluate afforded a white solid which was recrystalized from ethyl acetate to give naloxone (7a) as white needles, mp 181.5°–182° C. (lit.: Lewenstein supra, 184° C., lit.: Sankyo, Belg. Pat. No. 615,009 (1962) 177°–178° C.); yield 1.75 g (56%); tlc: single spot of $R_f$ 0.51. By concentration of the filtrate, a second crop of white needles was obtained; mp 180°–181.5° C.; yield 0.45 g (15%); tlc: single spot of $R_f$ 0.51. The main component (ca. ⅔) of the filtrate residue (0.33 g) was naloxone. Tlc indicated the presence of a single, faster moving contaminant ($R_f$ 0.75) whose NMR spectrum exhibited excess allyl absorption. (The NMR spectrum of the chloroform extract of the pH 13.5 solution above also contained excess allyl absorption and its tlc indicated the presence of naloxone and the $R_f$ 0.75 compound). The analysis sample of naloxone was prepared by recrystalization from ethyl acetate; mp 181°–182° C.

Calc. for $C_{19}H_{21}NO_4$: C, 69.71%; H, 6.47%; N, 4.28%. Found: C, 69.69%; H, 6.63%; N, 4.27%.

IR ($\mu$): 2.85 (sh), 2.90–3.18 (m), 3.58 (m), 5.81 (s), 6.11 (w), 6.20 (m); $CH_2Cl_2$.

NMR($\delta$): 6.8–6.4 (m), -6.2–4.9 (m, with medium broadened spike at 5.41), 4.69 (s), 3.7–1.2 (m); ratio 2:5:1:13; $CDCl_3$.

MS (m/e): 327.1457 (P, 33%, Calc. 327.1470), 58 (32%), 43 (100%).

Alkylation of noroxymorphone with cyclopropylcarbinyl bromide in hot ethanol using sodium bicarbonate as the acid scavenger similarly yielded N-cyclopropylmethylnoroxymorphone (same physical and spectral properties as those given in Example XVII below).

EXAMPLE XVII

N-CYCLOPROPYLMETHYLNOROXYMORPHONE (7b)

The crystalized N-cyclopropylmethylnoroxycodone (6b) (0.71 g, 0.002 mole) and pyridine hydrochloride (2.31 g, 0.02 mole) were thoroughly mixed in a small flask equipped with a micro distilling head. The flask was then immersed in an oil bath and heated with stirring (under nitrogen) to 193° C. and left at that temperature for 25 minutes. Then the temperature was raised to 210° C. over a ten minute period and kept at that temperature for five minutes. Next, the reaction vessel was withdrawn from the oil bath and allowed to cool. During the heating process, a small amount of pyridine distilled over. The syrup at high temperature became a semisolid mass when cooled. This was dissolved in 20 ml of water and the solution taken to pH 6–6.5 with aqueous 30% potassium hydroxide. After chloroform extraction (3 × 5 ml), the pH of the aqueous layer was raised to 13.5 with additional 30% potassium hydroxide. This solution was extracted with chloroform (3 × 8 ml) to remove any unreacted N-cyclopropylmethylnoroxycodone (6b). (After concentration, 0.04 g, 6%, of the starting material was recovered from this chloroform extract.) Next, the aqueous phase was acidified to pH 1 with concentrated hydrochloric acid, decolorized with Nuchar (Eastman, ca. 0.1g), filtered, and taken to pH 8.8 (pH meter) with concentrated aqueous ammonium hydroxide. The solution then was extracted with methylene chloride (3 × 50 ml) followed by chloroform (3 × 50 ml). The total, dried (over sodium sulfate) organic extract was evaporated at reduced pressure. The naltrexone (7b) thus isolated as an off-white solid was recrystalized from acetone; mp 173.5°–174.5° C. (lit. 168°–170° C.); yield 0.50 g (73%); tlc: single spot of $R_f$ 0.42; analysis sample mp 174.5°–175° C.

Calc. for $C_{20}H_{23}NO_4$: C, 70.36%; H, 6.79%; N, 4.10%. Found: C, 70.02%; H, 6.88%; N, 4.16%.

IR($\mu$): 2.84 (w), 2.94–3.15 (m), 3.58 (m), 5.79 (s), 6.11 (w), 6.19 (m); $CH_2Cl_2$.

NMR($\delta$): 6.8–6.4 (m), 6.02 (broadened s), 4.73 (s), 3.4–0.0 (m); ratio 2:2:1:18; $CDCl_3$.

MS(m/e): 341.1628 (P, 100%, Calc. 341.1626), 300.1213 (P-cyclopropyl, 26%, Calc. 300.1235), 110 (21%), 55 (50%).

EXAMPLE XVIII

N-ALLYLNOROXYMORPHONE (NALOXONE) (7a/7g) BY O-DEMETHYLATION

N-allylnoroxycodone (6g) (1.71 g, 0.005 mole) and pyridine hydrochloride (5.78 g, 0.05 mole) were thoroughly mixed in a 25 ml flask equipped with a stir bar and a short path distillation head. The flask was immersed in an oil bath and heated (under nitrogen) with stirring to 195° C. and left at that temperature for 20 minutes. The temperature was then raised to 205° C. over a five minute period and kept there for another five minutes. A few drops of pyridine distilled over during the heating process. Next, the semisolid mass from the cooled reaction vessel was dissolved in 40 ml of water. This solution was taken to pH 8.5-9.0 with concentrated ammonium hydroxide and then extracted with ether (6 × 50 ml). The ether solution was extracted first with aqueous sodium hydroxide (pH 13.1, 5 × 40 ml) and then with water (40 ml). Unreacted N-allylnoroxycodone, 0.09 g (5%), mp 134°-135° C., was recovered from the ether solution by concentration and recrystalization from ethanol. Next, the pH of the aqueous solution was lowered to 8.8 (pH meter) with aqueous 20% hydrochloric acid and the precipitated product was extracted into methylene chloride (6 × 40 ml). The methylene chloride solution was washed with water (50 ml), dried over sodium sulfate, and evaporated to a brown solid. This was dissolved in hot chloroform (10 ml) and passed through a short silica gel 60 column (hot chloroform as eluant) where most of the color was removed. Evaporation of the total eluate gave an off-white solid which was recrystalized from ethyl acetate; white needles of mp 181°-182° C. (lit.: Lewenstein supra 184° C., lit.: Seki supra 177°-178° C.); yield 0.48 g (29%); tlc: single spot of $R_f$ 0.51. By concentration of the filtrate a second crop was obtained; off-white needles of mp 179.5°-181.5° C.; yield 0.18 g (11%); tlc: single spot of $R_f$ 0.51. The filtrate residue (0.11 g) showed a single tlc spot of the same $R_f$, analysis sample mp 181°-182° C.; analytical and spectral data correspond with those obtained in Example XVI supra.

EXAMPLE XIX

CYCLOPROPANECARBOXYLIC ACID ANHYDRIDE

This was prepared from cyclopropanecarboxylic acid (Aldrich) and cyclopropanecarboxylic acid chloride (Aldrich) by the method given (Example IV) for the preparation of the cyclobutyl analogue and purified by vacuum distillation; bp 95°-100° C. at 6 torr (lit.: Castro and Dormoy, Bull. Soc. Chem. Fr. 8, 3034 (1971) bp 102°-104° C. at 8 torr); IR anhydride C=O stretch absorptions at 5.53 and 5.74μ.

EXAMPLE XX

14-CYCLOPROPYLCARBONYLOXYCODONE

This was prepared from oxycodone (6.31 g, 0.02 mole) and cyclopropane carboxylic acid anhydride (6.16 g, 0.04 mole) using the procedure outlined in Example III. After adjusting the pH to 11, the precipitated solid product was filtered, washed with cold water, dried in vacuo at room temperature and used without further purification; yield 7.73 g (99%); crude mp 169°-173° C. cor.; tlc: single spot of $R_f$ 0.60.

IR(μ): 3.56 (w), 3.61 (w), 3.65 (w), 5.76-5.87 (s, broad), 6.15 (w), 6.22 (m); $CH_2Cl_2$.

EXAMPLE XXI

N-VOC-14-CYCLOPROPYLCARBONYLNOROXYCODONE

This was prepared from the crude 14-cyclopropylcarbonyloxycodone (3.83 g, 0.01 mole) and vinyl chloroformate (0.03 mole) by the procedure given in Example VII. The crude title compound was obtained as an off-white foam which was used without further purification; weight 4.08 g, tlc: single spot of $R_f$ 0.72.

NMR(δ): 7.2-7.6 (m), 6.7-7.1 (m), 5.6-5.8 (broad), 3.9-5.1 (m with small spike at 4.82 and large spike at 4.00), 0.8-3.6 (m); ratio 1:2:1:7:14; $CDCl_3$.

Starting 14-cyclopropylcarbonyloxycodone (0.33 g) was recovered from the aqueous extracts.

EXAMPLE XXII

14-CYCLOPROPYLCARBONYLNOROXYCODONE HYDROCHLORIDE

Treatment of the crude N-VOC-14-cyclopropylcarbonylnoroxycodone (3.95 g, 0.009 mole) with anhydrous hydrogen chloride in methylene chloride according to the procedure in Example XI gave a tan foam which was refluxed for an hour in absolute methanol. Solvent evaporation at reduced pressure afforded the crude title compound as a tan solid; yield 3.62 g (99%). The remaining steps in the synthesis of naltrexone outlined in the accompanying patent application were performed using this material without further purification.

IR(μ): 3.56 (sh), 3.53-4.02 (m, broad), 5.74-5.84 (s, with 5.78 max), 6.12 (w), 6.22 (w); $CH_2Cl_2$.

NMR(δ): 10.9-9.4 (very broad), 6.95 (s), 5.2-4.8 (m, with spike at 4.90), 4.2-0.2 (m, with large spike at 4.01); ratio: 2:2:2:18, $CDCl_3$.

EXAMPLE XXIII

14-CYCLOPROPYLCARBONYLNOROXYCODONE ACETIC ACID SALT

Unpurified 14-cyclopropylcarbonyloxycodone (1.15 g, 0.003 mole) was heated in a 92° C. oil bath at 0.3 torr for two hours. Then the vacuum was replaced by a nitrogen atmosphere and after the oil bath had cooled to 65° C., 2,2,2-trichloroethyl chloroformate (0.006 mole) and 1,2-dichloroethane (10 ml) were added. The stirred, yellow solution was heated for 23 hours at 65° C. and then refluxed for an hour. The reddish glass obtained after vacuum evaporation was dissolved in ethyl acetate (75 ml), washed with 3 N hydrochloric acid (15 ml), water (15 ml), 5% aqueous sodium bicarbonate (15 ml), brine (15 ml), and dried over sodium sulfate. Rotary evaporation gave a tan foam which was dissolved in 5 ml of chloroform and eluted through a short silica gel 60 column using chloroform as the eluant. Evaporation of the eluate gave an off-white foam which was kept under vacuum at 60° C. for 40 hours at 0.4 torr. The tan solid which remained analyzed as a mixture of N-(2,2,2-trichloroethoxycarbonyl)-14-cyclopropylcarbonylnoroxycodone (tlc: single spot at $R_f$ 0.65) contaminated by trichloroethyl chloroformate.

IR (μ): 3.56 (w), 5.76 (sh), 5.80 (s), 5.86 (s), 6.13 (w); $CH_2Cl_2$ (chloroformate at 5.64[w]).

NMR(δ): 7.1-6.6 (m), 5.9-5.5 (broad), 5.2-0.7 (m with large spike at 4.01 and small spikes at 4.98 and 4.80); ratio: 2:1:21; $CDCl_3$ (chloroformate at 5.00).

All the unpurified N-trichloroethoxycarbonyl compound above was dissolved in 45 ml of aqueous 90% acetic acid. Zinc dust (1.44 g, 0.022 mole) was added in seven portions over a one hour period to the stirred mixture, to remove the N-trichloroethoxycarbonyl group and give the acetic acid salt of 14-cyclopropylcarbonylnoroxycodone (contaminated by zinc acetate and zinc chloride) on removal of the solvent acetic acid under high vacuum.

We claim:
1. Process of N-dealkylation of N-alkyl-14-hydroxymorphinans comprising the steps of
  (a) reacting an N-alkyl-14-acyloxymorphinan of the formula

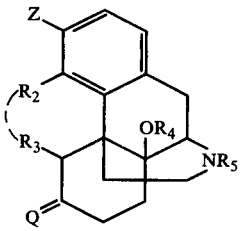

where Z is $R_1O$
where
  $R_1$ is lower alkanoyl of 1-6 carbon atoms wherein the alkyl moiety thereof is a straight chain or branch chain alkyl of 1-5 carbon atoms, phenyl lower alkanoyl wherein the alkyl moiety is as above, or cycloalkyl carbonyl having 3-6 carbon atoms in the cyclic moiety, straight chain or branch chain lower alkyl of 1-5 carbon atoms, cycloalkyl and cycloalkyl lower alkyl of 3-5 carbon atoms in the cyclic moiety and 1-5 carbon atoms in the lower alkyl moiety, phenyl lower alkyl and substituted phenyl lower alkyl wherein the lower alkyl is 1-5 carbon atoms and the substituents on the phenyl moiety are lower alkyl or lower alkoxy of 1-5 carbon atoms in the alkyl or alkoxy moiety,
  $R_2$ and $R_3$ are each hydrogen or taken together are oxa,
  $R_4$ is lower alkanoyl of 1-6 carbon atoms wherein the alkyl moiety thereof is straight or branch chain alkyl of 1-5 carbon atoms, or cycloalkylcarbonyl of 3-6 carbon atoms in the cyclic moiety, phenyl carbonyl, or substituted phenylcarbonyl, phenyl loweralkanoyl or substituted phenyl loweralkanoyl, wherein the alkanoyl moiety contains 1-6 carbon atoms, and the substituents on the phenyl moiety are loweralkyl or loweralkoxy of 1-5 carbon atoms,
  $R_5$ is lower alkyl of 1-6 carbon atoms, phenyl lower alkyl having 1-6 carbon atoms in the lower alkyl moiety, cycloalkyl or cycloalkyl lower alkyl of 3-6 carbon atoms in the cyclic moiety and 1-5 carbon atoms in the lower alkyl moiety,
  Q is two hydrogen atoms or oxo, With a source of the group Y—O—CO.— wherein Y is vinyl, 2-haloethyl, 2,2-dihaloethyl or 2,2,2-trihaloethyl to form the corresponding Y-oxycarbonylamide;
  (b) cleaving said Y-oxycarbonylamide under acidic conditions to split off said Y-oxycarbonyl group from the amino-N atom to obtain the corresponding secondary amine acid salt.

2. A process of claim 1 wherein Y is vinyl and step b) comprises reacting the vinyloxycarbonylamide thus formed with a hydrohalic acid and a hydroxylic reagent selected from the group consisting of water, lower carboxylic acid, and lower alkanol.

3. A process of claim 2 wherein $R_1$ is lower alkanoyl, cycloalkylcarbonyl or methyl, $R_5$ is methyl, Y is vinyl, the hydrohalic acid is selected from the group consisting of hydrogen chloride and hydrogen bromide, and the hydroxylic reagent is selected from the group consisting of methanol and ethanol.

4. A process of claim 2 in which the cleaving of said Y-oxycarbonylamide is carried out in the sequential stages consisting of the steps of:
  (a) reacting said Y-oxycarbonylamide with said hydrohalic acid in a reaction inert non-hydroxylic organic solvent,
  (b) removing the solvent and,
  (c) heating the residue in the alkanol.

5. A process according to claim 1 wherein Y is 2-haloethyl, 2,2-dihaloethyl or 2,2,2-trihaloethyl, where the halo moiety is chlorine or bromine, wherein step b) comprises cleaving the thus produced Y-oxycarbonylamide under acidic conditions in the presence of zinc and a hydroxylic solvent selected from the group consisting of carboxylic acids, water alkanols and mixtures thereof.

6. A process according to claim 5 wherein the carboxylic acids are lower alkanoic acids and the alkanols are lower alkanols of 1-5 carbon atoms in the alkyl moiety.

7. A compound of the formula:

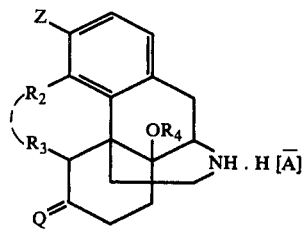

where $Z = R_1O$,
wherein
  $R_1, R_2, R_3, R_4$ and Q are as defined in claim 1 wherein [A] is the anion of any proton acid capable of forming acid addition salts with a secondary amine.

8. A compound of claim 7 wherein [A] is chloride, bromide, formate, acetate, benzene sulfonate, toluene sulfonate or methane sulfonate.

9. A compound of claim 7 wherein $R_1$ is acetyl, $R_4$ is acetyl, $R_2$ and $R_3$ taken together are oxa, and Q is oxo.

10. A compound of claim 7 wherein $R_1$ is methyl, $R_4$ is acetyl, $R_2$ and $R_3$ taken together are oxa, and Q is oxo.

11. A compound of claim 7 wherein $R_1$ is methyl, $R_4$ is cyclobutylcarbonyl or cyclopropylcarbonyl, $R_2$ and $R_3$ taken together are oxa and Q is oxo.

12. A process of reacting a compound of claim 7 wherein Z is $R_1O$ with aqueous mineral acid to form a compound of the formula

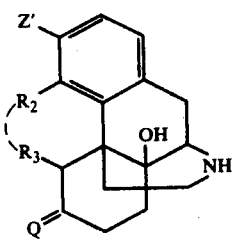

wherein $R_2$, $R_3$ and Q are as defined in claim 7, $Z'$ is = Z as defined in claim 7 wherein Z is $R_1O$ provided that where $R_1$ is alkanoyl, phenylalkanoyl or cycloalkyl carbonyl, then $Z'$ is hydroxyl.

13. A process according to claim 12 wherein $R_1$ is acetyl, $R_4$ is acetyl, $R_2$ and $R_3$ taken together are oxa, Q is oxo, and $Z'$ is hydroxyl.

14. A process according to claim 12 wherein $R_1$ is methyl, $R_4$ is acetyl, $R_2$ and $R_3$ taken together are oxa, Q is oxo, and $Z'$ is —O—methyl.

* * * * *